(12) United States Patent
Rothermel et al.

(10) Patent No.: US 9,744,326 B2
(45) Date of Patent: Aug. 29, 2017

(54) ADJUSTABLE LOCKING FOREHEAD SUPPORT FOR A PATIENT INTERFACE DEVICE

(75) Inventors: Justin Edward Rothermel, Monroeville, PA (US); Justin Eric Angert, Pittsburgh, PA (US); Robert Earl Hieber, IV, Export, PA (US); Richard Thomas Haibach, Pittsburgh, PA (US); Chad Zediker, Greensburg, PA (US)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 426 days.

(21) Appl. No.: 14/117,483

(22) PCT Filed: Apr. 26, 2012

(86) PCT No.: PCT/IB2012/052083
§ 371 (c)(1),
(2), (4) Date: Nov. 13, 2013

(87) PCT Pub. No.: WO2012/156845
PCT Pub. Date: Nov. 22, 2012

(65) Prior Publication Data
US 2014/0230820 A1 Aug. 21, 2014

Related U.S. Application Data

(60) Provisional application No. 61/486,807, filed on May 17, 2011.

(51) Int. Cl.
*A62B 18/02* (2006.01)
*A61M 16/06* (2006.01)
*A61M 16/00* (2006.01)

(52) U.S. Cl.
CPC .... *A61M 16/0655* (2014.02); *A61M 16/0057* (2013.01); *A61M 16/06* (2013.01); *A61M 16/0622* (2014.02); *A61M 16/0683* (2013.01)

(58) Field of Classification Search
CPC ......... A62B 18/02; A62B 18/08; A62B 18/25; A61M 15/00; A61M 16/00; A61M 16/06;
(Continued)

(56) References Cited

U.S. PATENT DOCUMENTS

2007/0107733 A1  5/2007  Ho
2011/0094516 A1  4/2011  Chang

FOREIGN PATENT DOCUMENTS

EP  1493461 A2  1/2005
EP  2005985 A2  12/2008
(Continued)

*Primary Examiner* — Peter S Vasat
(74) *Attorney, Agent, or Firm* — Michael W. Haas

(57) ABSTRACT

A patient interface device (8) includes a patient sealing assembly (12) including a cushion (14) and a frame member (16), and an adjustable forehead support assembly (26) provided at the distal end (24) of the frame member. The assembly includes an adjustment mechanism (28) coupled to a forehead cushion (30), the adjustment mechanism including a housing (32), a forehead cushion support member (52) having a base portion (58) and an elongated post member (60) extending from the base portion and received within the housing, and a locking member (54, 56) structured to be selectively coupled to the elongated post member. In the locked condition, the locking member engages the elongated post member and prevents the elongated post member from moving relative to the housing, and in the unlocked condition the locking member does not engage the elongated post member such that the elongated post member and the housing are freely linearly movable with respect to one another.

10 Claims, 20 Drawing Sheets

(58) Field of Classification Search
CPC .......... A61M 16/0622; A61M 16/0655; A61M 16/0683; A61M 16/0633; A61M 16/0638; A61M 16/0644; A61M 16/065; B63C 11/24
See application file for complete search history.

(56) References Cited

FOREIGN PATENT DOCUMENTS

| | | |
|---|---|---|
| WO | WO2004078231 A2 | 9/2004 |
| WO | WO2005009521 A1 | 2/2005 |
| WO | WO2005123166 A1 | 12/2005 |
| WO | WO2006074517 A1 | 7/2006 |
| WO | WO2007143793 A1 | 12/2007 |
| WO | WO2010133218 A2 | 11/2010 |

# ADJUSTABLE LOCKING FOREHEAD SUPPORT FOR A PATIENT INTERFACE DEVICE

CROSS-REFERENCE TO RELATED APPLICATIONS

This patent application claims the priority benefit under 35 U.S.C §371 of international patent application no. PCT/IB2012/052083, filed Apr. 26, 2012, which claims the priority benefit under 35 U.S.C. §119(e) of U.S. Provisional Application No. 61/486,807 filed on May 17, 2011, the contents of which are herein incorporated by reference.

BACKGROUND OF THE INVENTION

1. Field of the Invention

The present invention relates to patient interface devices for transporting a gas to and/or from an airway of a user, and in particular, to a patient interface device including a mechanism for adjusting a forehead support of the patient interface device.

2. Description of the Related Art

There are numerous situations where it is necessary or desirable to deliver a flow of breathing gas non-invasively to the airway of a patient, i.e., without intubating the patient or surgically inserting a tracheal tube in their esophagus. For example, it is known to ventilate a patient using a technique known as non-invasive ventilation. It is also known to deliver continuous positive airway pressure (CPAP) or variable airway pressure, which varies with the patient's respiratory cycle, to treat a medical disorder, such as sleep apnea syndrome, in particular, obstructive sleep apnea (OSA), or congestive heart failure.

Non-invasive ventilation and pressure support therapies involve the placement of a patient interface device including a mask component on the face of a patient. The mask component may be, without limitation, a nasal mask that covers the patient's nose, a nasal cushion having nasal prongs that are received within the patient's nares, a nasal/oral mask that covers the nose and mouth, or a full face mask that covers the patient's face. The patient interface device interfaces the ventilator or pressure support device with the airway of the patient, so that a flow of breathing gas can be delivered from the pressure/flow generating device to the airway of the patient. It is known to maintain such devices on the face of a wearer by a headgear having one or more straps adapted to fit over/around the patient's head.

Because such patient interface devices are typically worn for an extended period of time, it is important for the headgear to maintain the mask component of the device in a tight enough seal against the patient's face without discomfort. One area where fit and comfort is often a concern is the bridge of the patient's nose, as most patient interface devices will apply a pressure to this area. If this pressure is not able to be managed effectively, either or both of a poor fit or patient discomfort will result, thereby limiting the effectiveness of the device.

SUMMARY OF THE INVENTION

Accordingly, it is an object of the present invention to provide a patient interface device that overcomes the shortcomings of conventional patient interface devices. This object is achieved according to one embodiment of the present invention by providing a patient interface device that includes a selectively adjustable forehead support assembly that allows for simple and convenient management of the nose bridge pressure that is applied by the patient interface device.

In one embodiment, a patient interface device is provided that includes a patient sealing assembly for delivering a flow of breathing gas to an airway of the patient, the patient sealing assembly including a cushion and a frame member coupled to the cushion, and an adjustable forehead support assembly provided at the distal end of the frame member. The adjustable forehead support assembly includes an adjustment mechanism coupled to a forehead cushion. The adjustment mechanism includes a housing, a forehead cushion support member having a base portion coupled to the forehead cushion and an elongated post member extending from the base portion and received within the housing, and a locking member structured to be selectively coupled to the elongated post member. The locking member is moveable between a locked condition and an unlocked condition. In the locked condition, the locking member engages the elongated post member and prevents the elongated post member from moving relative to the housing. In the unlocked condition, the locking member does not engage the elongated post member such that the elongated post member and the housing are freely linearly movable with respect to one another in a direction along a longitudinal axis of the elongated post member without any spring bias being applied to the elongated post member along the longitudinal axis, and wherein movement of the elongated post member relative to the housing causes movement of the frame member and the cushion relative to the forehead cushion.

In another embodiment, a patient interface device is provided that includes a patient sealing assembly adapted to communicate a flow of breathing gas within an airway of a patient, the patient sealing assembly including a cushion and a frame member coupled to the cushion. The patient interface device also includes an adjustable forehead support assembly provided at a distal end of the frame member, the adjustable forehead support assembly including an adjustment mechanism coupled to a forehead cushion. The adjustment mechanism includes a housing and a forehead cushion support member having a base portion coupled to the forehead cushion and an elongated post member extending from the base portion and received within the housing, wherein the housing includes a rear end having a rear orifice and a pawl member. The elongated post member is received through the rear orifice and includes a first gear train and a second gear train each provided along at least a portion of a length of the elongated post member. The adjustment mechanism further includes a knobbed actuator having a pinion member. The pinion member is in operative engagement with the first gear train. The pawl member is biased to normally be in engagement with the second gear train. Movement of the knobbed actuator in a direction transverse to a longitudinal axis of the elongated post member causes the pawl member to be moved out of engagement with the second gear train such that rotation of the knobbed actuator causes relative movement between the elongated post member and the housing along a longitudinal axis of the elongated post member. Movement of the elongated post member relative to the housing causes movement of the frame member and the cushion relative to the forehead cushion.

These and other objects, features, and characteristics of the present invention, as well as the methods of operation and functions of the related elements of structure and the combination of parts and economies of manufacture, will become more apparent upon consideration of the following description and the appended claims with reference to the accompanying drawings, all of which form a part of this specification, wherein like reference numerals designate corresponding parts in the various figures. It is to be expressly understood, however, that the drawings are for the purpose of illustration and description only and are not intended as a definition of the limits of the invention.

DETAILED DESCRIPTION OF EXEMPLARY EMBODIMENTS

Figure 1:
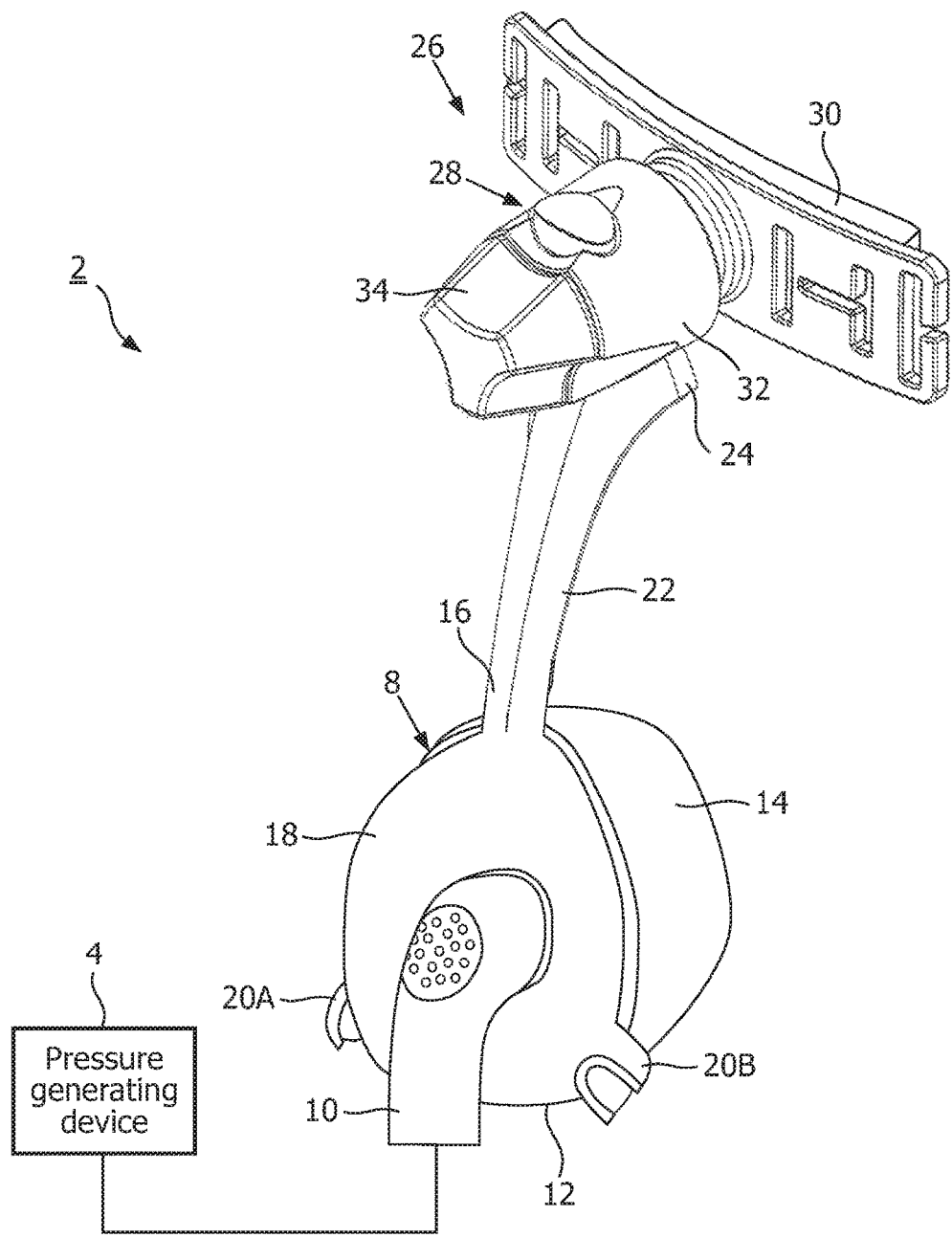
FIGS. 1 and 2 are isometric and side schematic diagrams, respectively, of a system adapted to provide a regimen of respiratory therapy to a patient according to one exemplary embodiment of the present invention.

As used herein, the singular form of "a", "an", and "the" include plural references unless the context clearly dictates otherwise. As used herein, the statement that two or more parts or components are "coupled" shall mean that the parts are joined or operate together either directly or indirectly, i.e., through one or more intermediate parts or components, so long as a link occurs. As used herein, "directly coupled" means that two elements are directly in contact with each other. As used herein, "fixedly coupled" or "fixed" means that two components are coupled so as to move as one while maintaining a constant orientation relative to each other.

As used herein, the word "unitary" means a component is created as a single piece or unit. That is, a component that includes pieces that are created separately and then coupled together as a unit is not a "unitary" component or body. As employed herein, the statement that two or more parts or components "engage" one another shall mean that the parts exert a force against one another either directly or through one or more intermediate parts or components. As employed herein, the term "number" shall mean one or an integer greater than one (i.e., a plurality).

Directional phrases used herein, such as, for example and without limitation, top, bottom, left, right, upper, lower, front, back, and derivatives thereof, relate to the orientation of the elements shown in the drawings and are not limiting upon the claims unless expressly recited therein.

Figure 2:
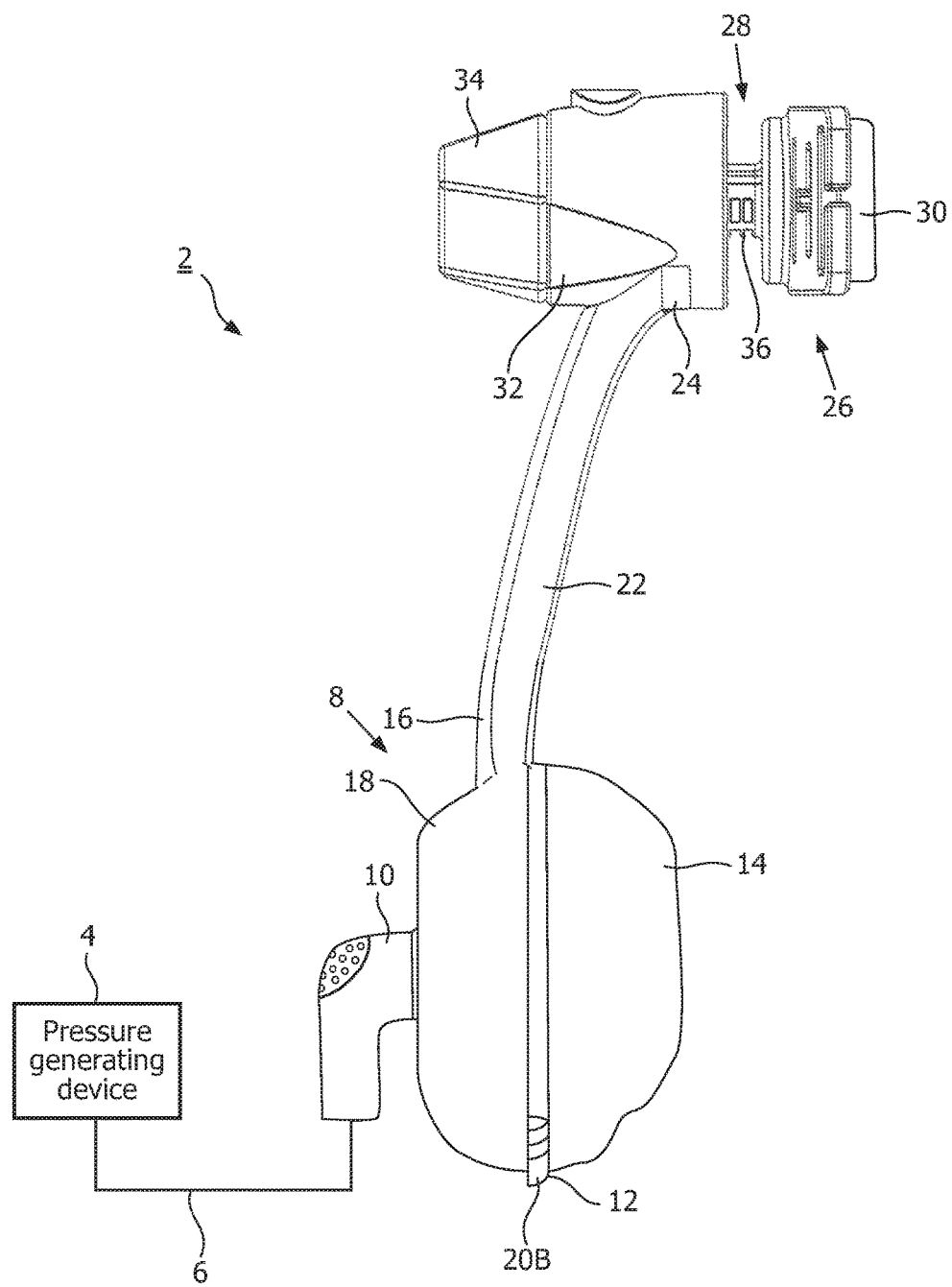

A system 2 adapted to provide a regimen of respiratory therapy to a patient according to one exemplary embodiment is generally shown in FIGS. 1 and 2. System 2 includes a pressure generating device 4, a delivery conduit 6, and a patient interface device 8 having a fluid coupling conduit 10. Pressure generating device 4 is structured to generate a flow of breathing gas and may include, without limitation, ventilators, constant pressure support devices (such as a continuous positive airway pressure device, or CPAP device), variable pressure devices (e.g., BiPAP®, Bi-Flex®, or C-Flex™ devices manufactured and distributed by Philips Respironics of Murrysville, Pa.), and auto-titration pressure support devices. Delivery conduit 6 is structured to communicate the flow of breathing gas from pressure generating device 4 to patient interface device 8 through fluid coupling conduit 10, which in the illustrated embodiment is an elbow connector. Delivery conduit 6 and patient interface device 8 are often collectively referred to as a patient circuit.

Patient interface device 8 includes a patient sealing assembly 12, which in the illustrated embodiment is a nasal mask. However, other types of patient sealing assemblies, such as, without limitation, a nasal/oral mask, a nasal cushion (such as a "pillows-style" nasal cushion or an "under the nose style" nasal cushion), or a full face mask, which facilitates the delivery of the flow of breathing gas to the airway of a patient may be substituted for patient sealing assembly 12 while remaining within the scope of the present invention. Patient sealing assembly 12 includes a cushion 14 coupled to a frame member 16. In the illustrated embodiment, cushion 14 is defined from a unitary piece of soft, flexible, cushiony, elastomeric material, such as, without limitation, silicone, an appropriately soft thermoplastic elastomer, a closed cell foam, or any combination of such materials.

Also in the illustrated embodiment, frame 16 is made of a rigid or semi-rigid material, such as, without limitation, an injection molded thermoplastic or silicone, and includes a faceplate portion 18 to which cushion 14 is fluidly attached. An opening in faceplate portion 18, to which fluid coupling conduit 10 is coupled, allows the flow of breathing gas from pressure generating device 4 to be communicated to an interior space defined by cushion 14, and then to the airway of a patient. In an alternative embodiment, cushion 14 may be supported by and received through an orifice in frame 16 so that fluid couple conduit can be directly connected to cushion 14 rather than to a faceplate portion. In addition, in the exemplary embodiment, faceplate portion 18 includes first and second socket type connecting members 20A, 20B for receiving a ball connector of a respective strap of a headgear component (not shown) to secure patient interface device 8 to the patient's head.

Frame member 16 also includes an elongated connecting member 22 having a distal end 24 that is connected to an adjustable forehead support assembly 26 of patient interface device 8. It is to be understood that connecting member 32 can have a variety of different sizes, shapes, and configurations, and can be coupled to the frame at any location. Adjustable forehead support assembly 26 includes an adjustment mechanism 28 that is coupled to a forehead cushion 30, which in the exemplary embodiment is made of a material that is similar to the material of cushion 14. As described in detail herein, adjustment mechanism 28 provides a mechanism for selectively adjusting the force applied to the bridge of the nose of a patient by an apex portion of cushion 14 by varying the position of connecting member 22, and in particular distal end 24 thereof, with respect to forehead cushion 30.

In the illustrated embodiment, adjustment mechanism 28 includes a housing 32 coupled to distal end 24 of connecting member 22, a cap 34 coupled to housing 32, and a linear translation assembly 36 (described in greater detail below) partially received and housed within housing 32. While in the illustrated embodiment housing 32 is formed separately and attached to frame member 16 by a suitable mechanism such as an adhesive, in alternative embodiments it may also be formed as an integral part of frame member 16.

Figure 3:
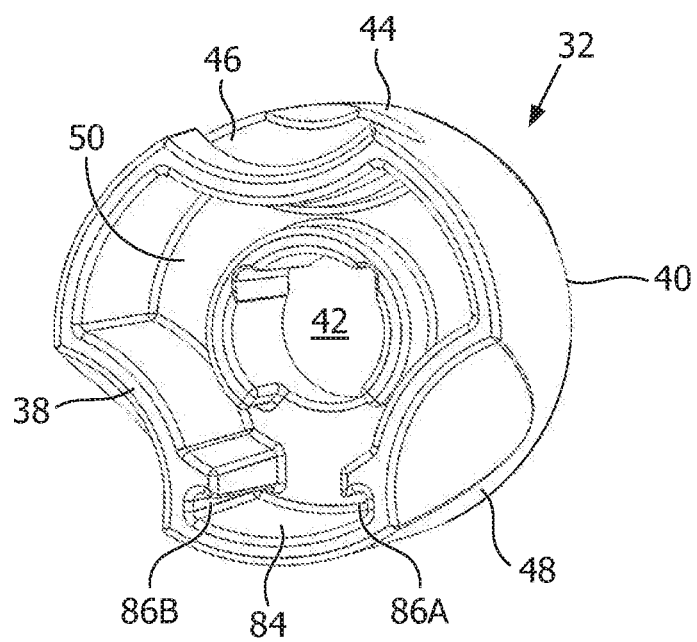
FIG. 3 is a front isometric view of a housing forming part of the patient interface device of the system of FIG. 1.

FIG. 3 is a front isometric view of housing 32. As seen in FIG. 3, housing 32 includes a front end 38 to which cap 34 is attached, and a rear end 40 having an orifice 42 formed therein. Housing 32 also includes a top surface 44 having an orifice 46 formed therein, and a bottom surface 48 to which distal end 24 of connecting member 22 is attached (or formed as an integral part thereof as discussed above). In addition, housing 32 defines an inner chamber 50.

Figure 4:
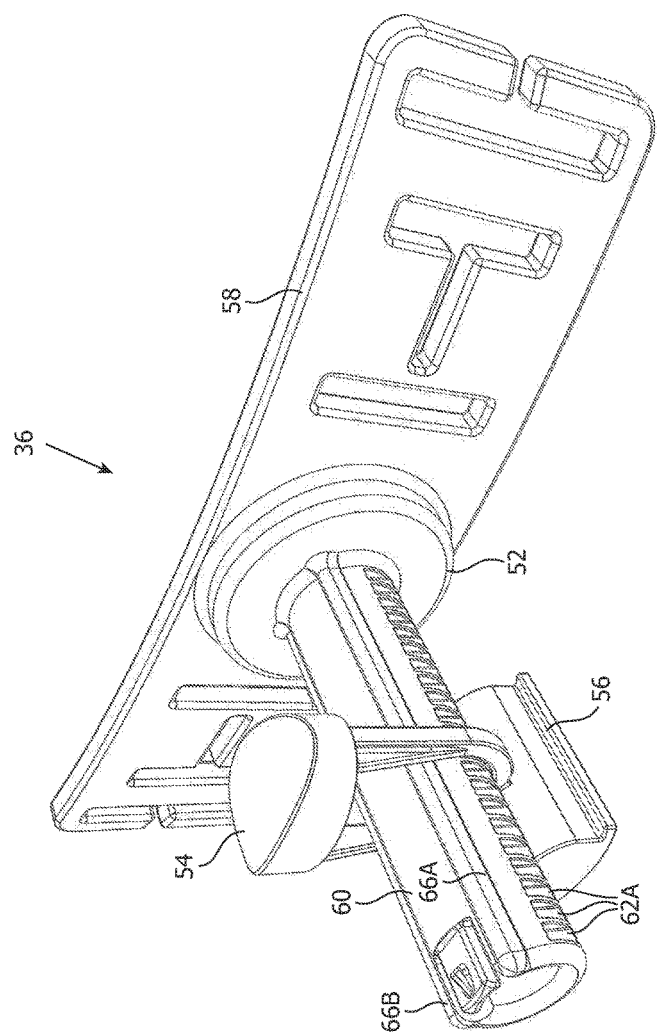
FIG. 4 is a front isometric view of a linear translation assembly forming part of the patient interface device of the system of FIG. 1.

FIG. 4 is an isometric view of linear translation assembly 36. Linear translation assembly 36 includes a forehead cushion support member 52, a button member 54, and a bumper member 56.

Figure 5:
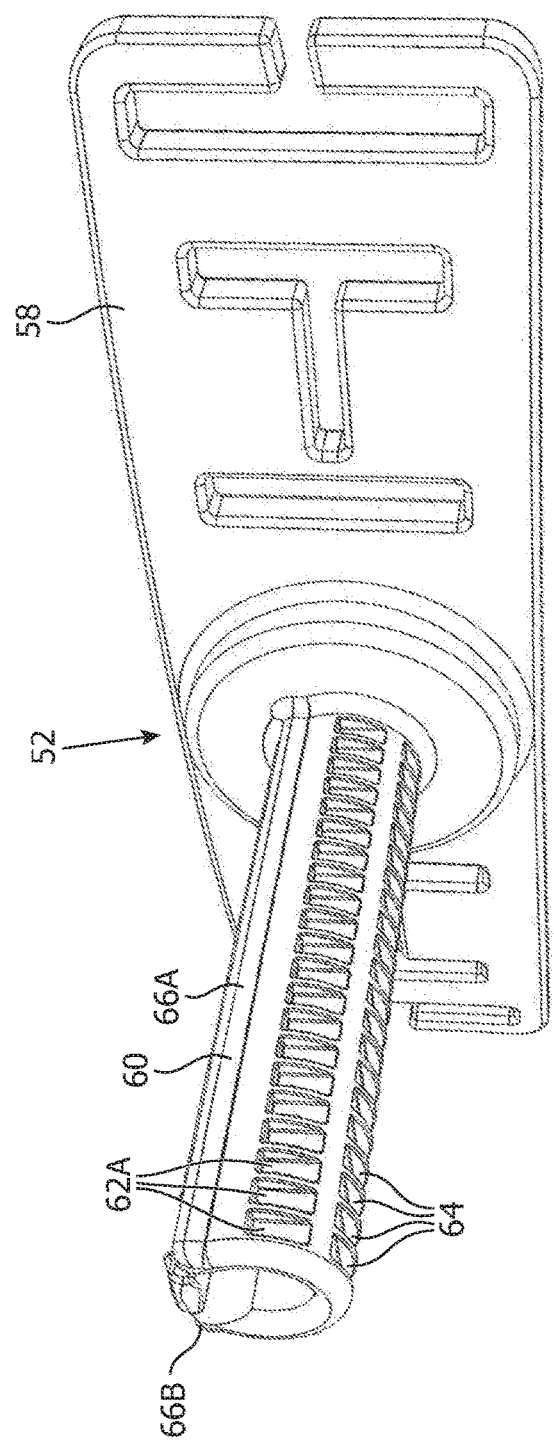
FIGS. 5 and 6 are front isometric and bottom plan views, respectively, of a forehead cushion support member forming part of the patient interface device of the system of FIG. 1.
Figure 6:
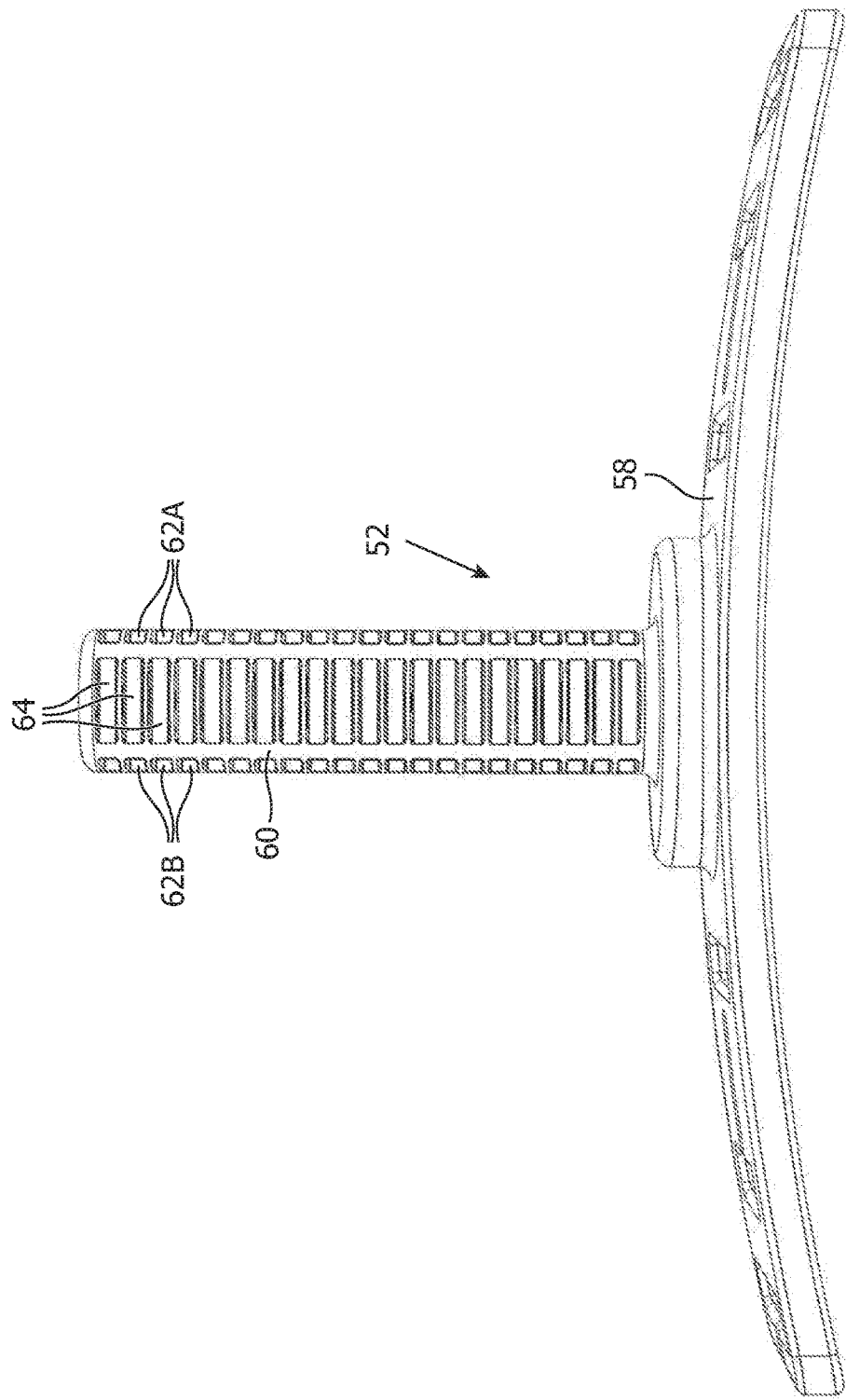

FIG. 5 is an isometric view and FIG. 6 is a bottom elevational view of forehead cushion support member 52. As seen in FIG. 5, forehead cushion support member 52 includes a base portion 58 to which forehead cushion 30 is attached, and an elongated post member 60 extending from base portion 58. In the illustrated, non-limiting embodiment, post member 60 includes side recesses 62A, 62B on the right and left sides, respectively, thereof, and a bottom recesses 64 on the bottom surface thereof. It will be appreciated, however, that other recess shapes and configurations are also possible. For example, a plurality of C-shaped recesses could be provided on post member 60 that each span both the bottom and the sides thereof. Alternatively, just two rather than three sets of recesses (e.g., just sides recesses 62A, 62B) may also be employed. Post member 60 further includes rounded top edges 66A, 66B (FIG. 4). These features (rounded top edges 66A, 66B) help "key" the assembly to keep it from rotating and help it maintain orientation during assembly.

Figure 7:
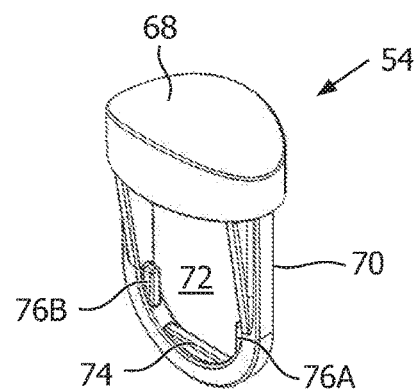
FIG. 7 is a front isometric view of a button member forming part of the patient interface device of the system of FIG. 1.

FIG. 7 is an isometric view of button member 54. As seen in FIG. 7, button member 54 includes a top engagement portion 68 and a looped portion 70 defining an orifice 72 extending downwardly from engagement portion 68. In addition, looped portion 70 includes a bottom projecting member 74 and right and left side projecting members 76A, 76B, respectively. It will be appreciated, however, that other projecting shapes and configurations are also possible.

Figure 8:
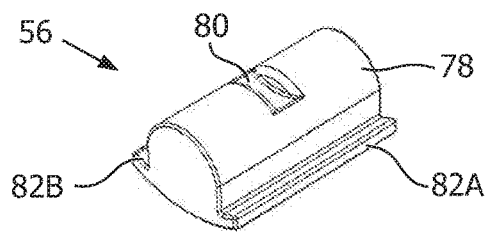
FIG. 8 is a front isometric view of a bumper member forming part of the patient interface device of the system of FIG. 1.

FIG. 8 is an isometric view of bumper member 56 according to one exemplary, non-limiting embodiment. In the exemplary embodiment, bumper member 56 is made of a flexible, elastic material, such as, without limitation, silicone. Bumper member 56 includes a central portion 78 having a recess 80 provided in the rounded top surface thereof. Bumper member 56 also includes outwardly extending flanges 82A, 82B provided on opposites sides of the bottom surface thereof. In alternative embodiments, recess 80 may be omitted, in which case the bumper could be a simple extruded shape. Also, the top surface of the bumper may take on other shapes (i.e., other than round).

Figure 9:
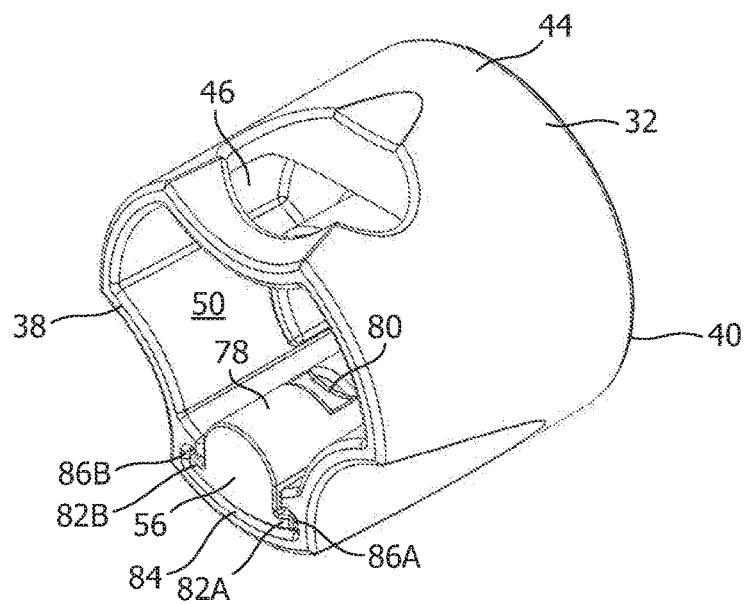
FIG. 9 is a front isometric view of the bumper member received within the housing forming part of the patient interface device of the system of FIG. 1.

In order to assemble adjustment mechanism 28, bumper member 56 is inserted into inner chamber 50 of housing 32 as shown in FIG. 9. In particular, the bottom surface of bumper member is received within bottom slot 84 of housing 32, with flanges 82A, 82B being received within end slot portion 86A, 86B. When bumper member 56 is positioned in this manner, recess 80 will be positioned beneath orifice 46 of housing 32. Button member 54 is then inserted into inner chamber 50 through orifice 46 looped portion 70 end first so that that the bottom of looped portion 70 is received within recess 80. Recess 80 provides a centering function to help to ensure that button member 54 is properly aligned and received. A downward force is then applied to engagement portion 68 of button member 54, thereby compressing bumper member 56. When this is done, post member 60 is inserted through orifice 42 of housing 32 and through looped portion 70 of button member 54.

As will be appreciated, the act of applying the downward force to button member 54 will provided clearance for post member 60 by moving projecting members 74, 76A, and 76B out of the path thereof. When the downward force is removed, bumper member 56 will decompress, and button member will be forced upwardly, causing projecting members 74, 76A, and 76B to be received within respective recesses 62A, 62B, and 64 of post member 60 (fixing it in place). Post member 60 may thus be selectively moved linearly relative to button member 54 and bumper member 56 (and thus housing 32) by pressing button member 54 as just described, moving post member 60 to a desired location, and releasing the pressure from button member 56 to allow projecting members 74, 76A, and 76B to be received within the respective recesses 62A, 62B, and 64 with which that they are then aligned.

Thus, when patient interface device 8 is assembled as shown in FIGS. 1 and 2, the position of housing 32 and connecting member 22 of frame member 16 relative to forehead cushion support member 52 and forehead cushion 30 (which will be at a fixed position on the patient's head) can be linearly adjusted by operation of the adjustment mechanism 28 as just described. This linear adjustment action allows for selective adjustment of the force that is applied to the bridge of the patient's nose by the apex portion of cushion 14 because varying the position of connecting member 22 as just described will cause the apex portion of cushion 14 to rotate toward and away from the patient's nose.

Figure 10:
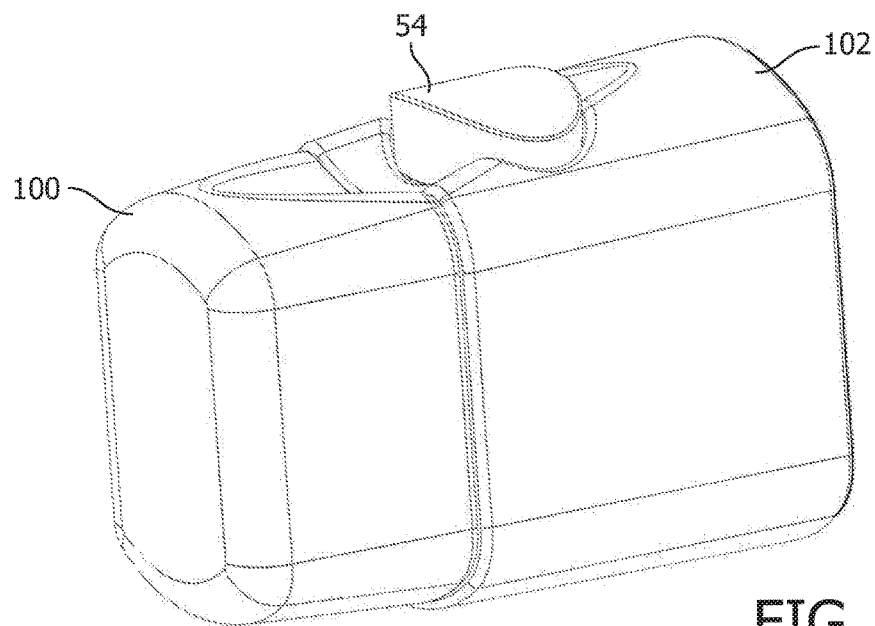
FIG. 10 is an isometric view showing an alternative cap and housing forming part of the patient interface device of the system of FIG. 1 according to an alternative embodiment.
Figure 11:
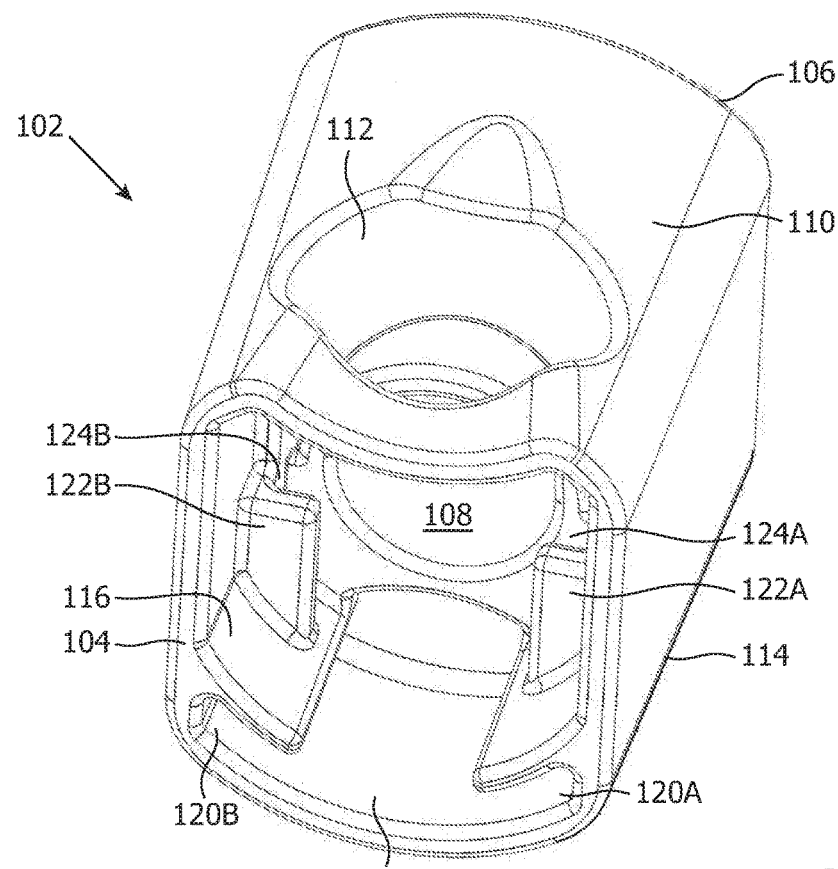
FIG. 11 is a front isometric view and FIG. 12 is a top plan view of the housing of FIG. 10.
Figure 12:
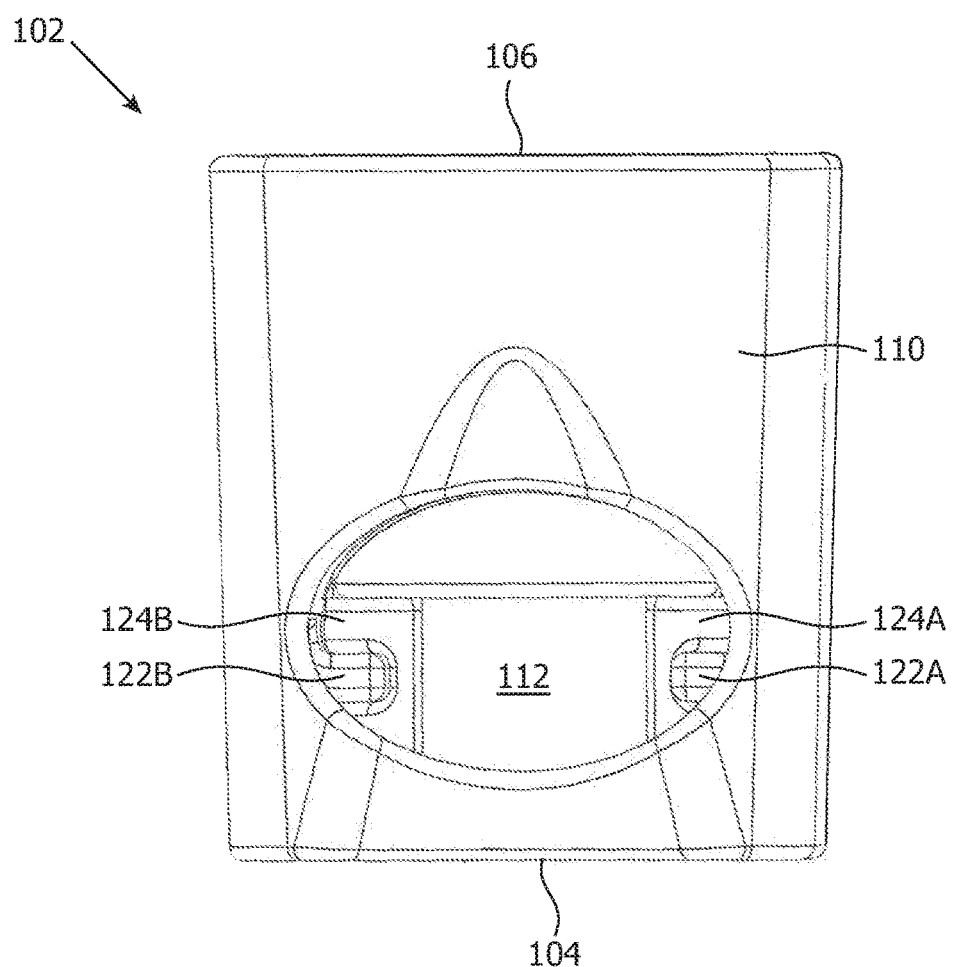
Figure 13:
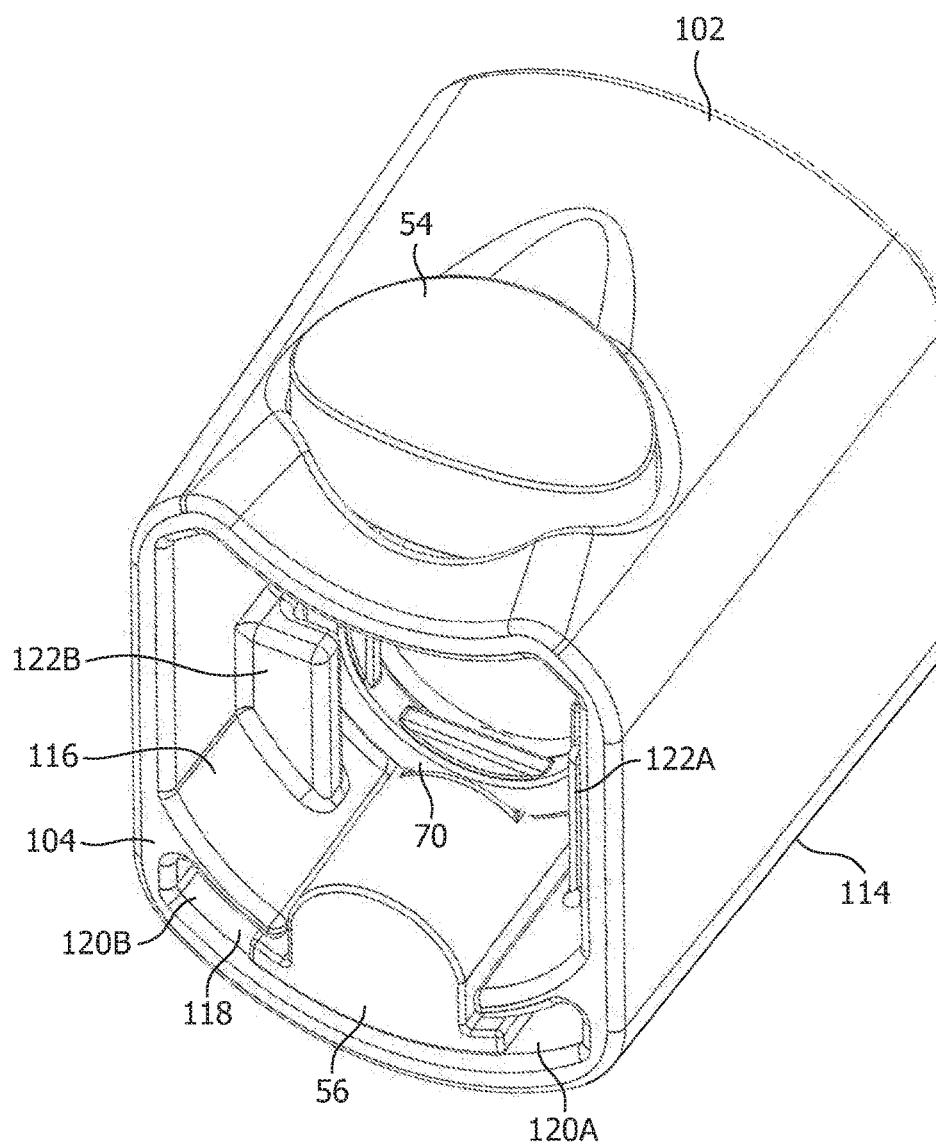
FIG. 13 is a front isometric view of the housing of FIG. 10 showing a partially assembled linear translation assembly.

FIG. 10 is an isometric view showing an alternative cap 100 and housing 102 that may be used to house linear translation assembly 36 in adjustable forehead support assembly 26. Like housing 32 described elsewhere herein, housing 102 is structured to be coupled to distal end 24 of connecting member 22. FIG. 11 is a front isometric view and FIG. 12 is a top plan view of housing 102. As seen in FIGS. 11 and 12, housing 102 includes a front end 104 to which cap 100 is attached, and a rear end 106 having an orifice 108 formed therein. Housing 102 also includes a top surface 110 having an orifice 112 formed therein, and a bottom surface 114 to which distal end 24 of connecting member 22 is attached (or formed as an integral part thereof as discussed above). Housing 102 defines an inner chamber 116, and includes a bottom slot 118 having end slot portions 120A, 120B. In addition, wall members 122A, 122B are provided on opposite sides of inner chamber 116, and define receiving slots 124A, 124B. As seen in FIG. 13, when linear translation assembly 36 is assembled using housing 102, looped portion 70 of button member 54 is received and retained within receiving slots 124A, 124B. In this manner, receiving slots 124A, 124B help to control the angle of button member 54 when depressed and in use.

Figure 14:
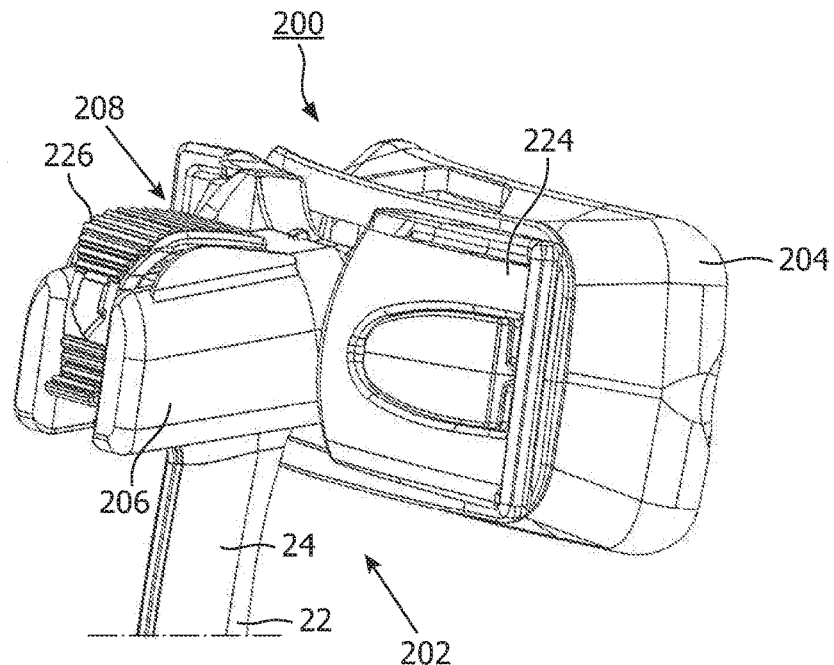
FIG. 14 is a front isometric view and FIG. 15 is a side elevational view of an adjustable forehead support assembly according to an alternative embodiment of the present invention.
Figure 15:
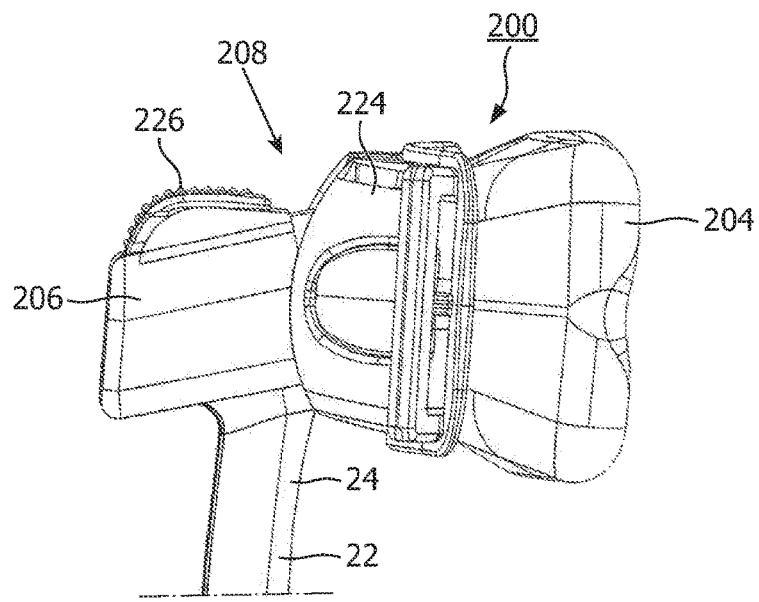
Figure 16:
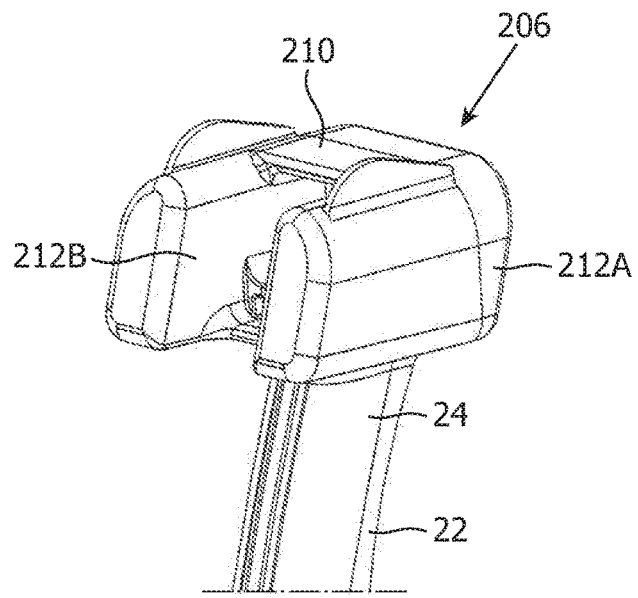
FIGS. 16, 17, 18, and 19 are front isometric, rear isometric, front elevational and rear elevational views, respectively, of a housing of the adjustable forehead support assembly shown in FIGS. 14 and 15.
Figure 17:
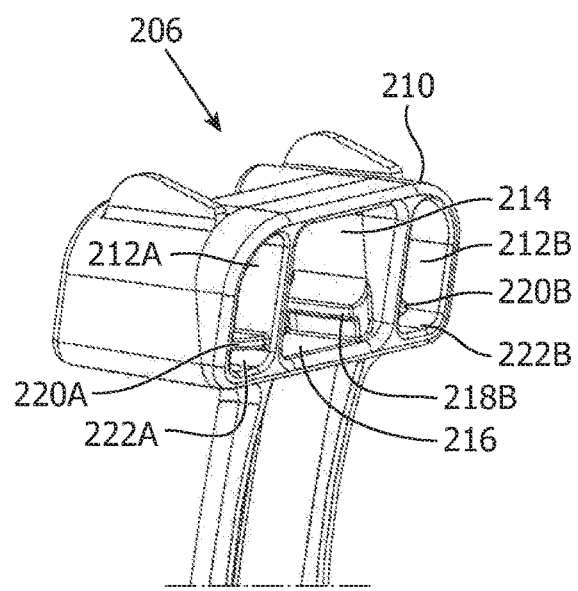
Figure 18:
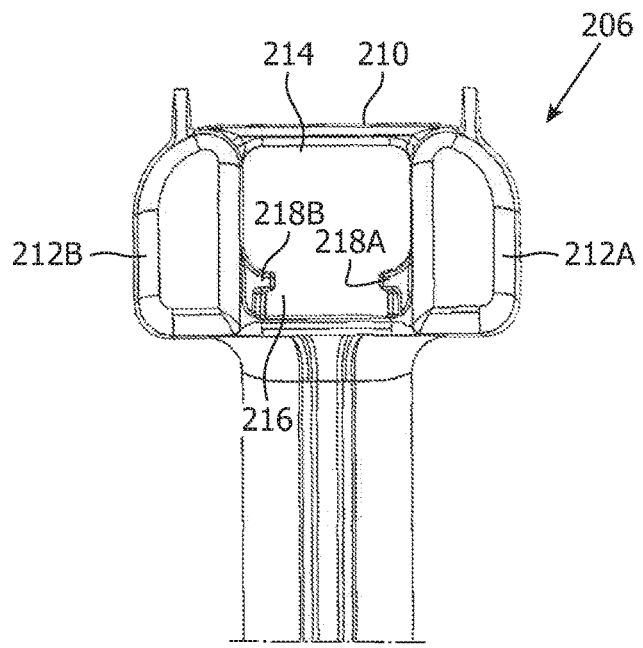
Figure 19:
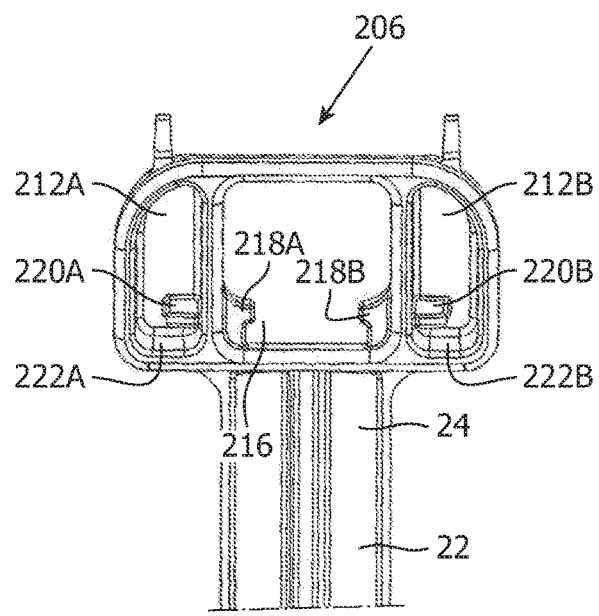

FIG. 14 is a front isometric view and FIG. 15 is a side elevational view of an alternative adjustable forehead support assembly 200 that may be substituted for adjustable forehead support assembly 26 in patient interface device 8. Adjustable forehead support assembly 200 includes an adjustment mechanism 202 that is coupled to a forehead cushion 204, which in the exemplary embodiment is made of a material that is similar to the material of cushion 14. As described in detail herein, adjustment mechanism 202 provides a mechanism for selectively adjusting the force applied to the bridge of the nose of a patient by an apex portion of cushion 14 by varying the position of connecting member 22, and in particular distal end 24 thereof, with respect to forehead cushion 204. In the illustrated embodiment, adjustment mechanism 202 includes a housing 206 coupled to distal end 24 of connecting member 22, and a linear translation assembly 208 (described in greater detail below) partially received and housed within housing 206. While in the illustrated embodiment housing 206 is formed as an integral part of frame member 16, it may also be formed separately and attached to frame member 16 by a suitable mechanism such as an adhesive.

FIGS. 16, 17, 18, and 19 are front isometric, rear isometric, front elevational and rear elevational views, respectively, of housing 206 (shown attached to distal end 24 of frame member 16). As seen in FIGS. 16, 17, 18, and 19, housing 206 includes a main body having a first side channel 212A and a second side channel 212B located on opposite sides of a main channel 214. In the illustrated embodiment, first side channel 212A and second side channel 212B are each open at one end thereof and closed at the opposite end thereof, and main channel 214 extends entirely through main body 210. In addition, main channel 214 includes a lower slot 216 defined by flange members 218A, 218B, and each side channel 212A, 212B includes a flange member 220A, 220B defining a slot 222A, 222B.

Linear translation assembly 208 includes a forehead cushion support member 224 and a button assembly 226. Forehead cushion support member 224 and button assembly 226 are each described in detail below.

Figure 20:
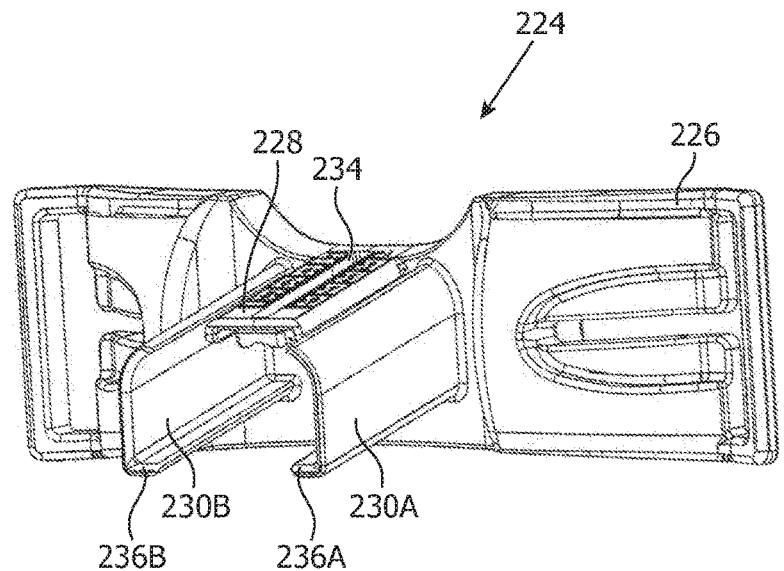
FIGS. 20 and 21 are front isometric and bottom elavational views, respectively, of a forehead cushion support member according to the principles of the present invention.
Figure 21:
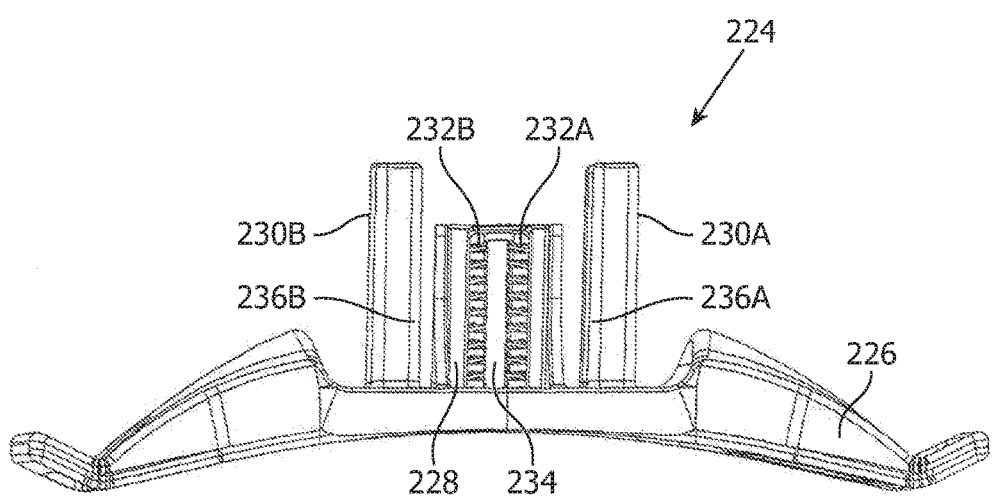

FIG. 20 is a front isometric view and FIG. 21 is a bottom elevational view of forehead cushion support member 224 according to the exemplary embodiment. Forehead cushion support member 224 includes a base portion 226 to which forehead cushion 204 is attached, an elongated central post member 228 extending from a central region of base portion 226, and first and second elongated side post members 230A, 230B extending from base portion 226 on either side of central post member 228. In the exemplary embodiment, central post member 228 includes a row of teeth 232A and a row of teeth 232B on the bottom surface thereof located on opposite sides of a central orifice 234 extending through central post member 228. In addition, side post members 230A, 230B each include a lower flange 236A, 236B. The function of these components is described below.

Figure 22:
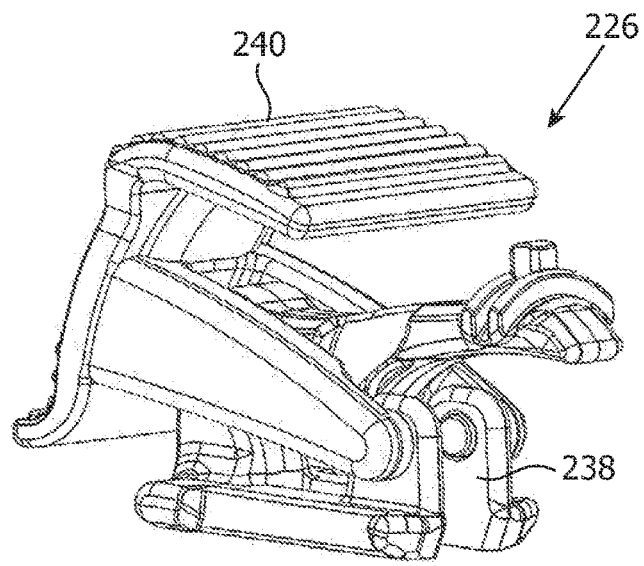
FIG. 22 is a front isometric view of a button assembly of the adjustable forehead support assembly shown in FIGS. 14 and 15.

FIG. 22 is a front isometric view of an exemplary embodiment of button assembly 226 of linear translation assembly 208. Button assembly 226 includes two cooperating components, a base member 238 and a button member 240, each of which is described in detail below.

Figure 23:
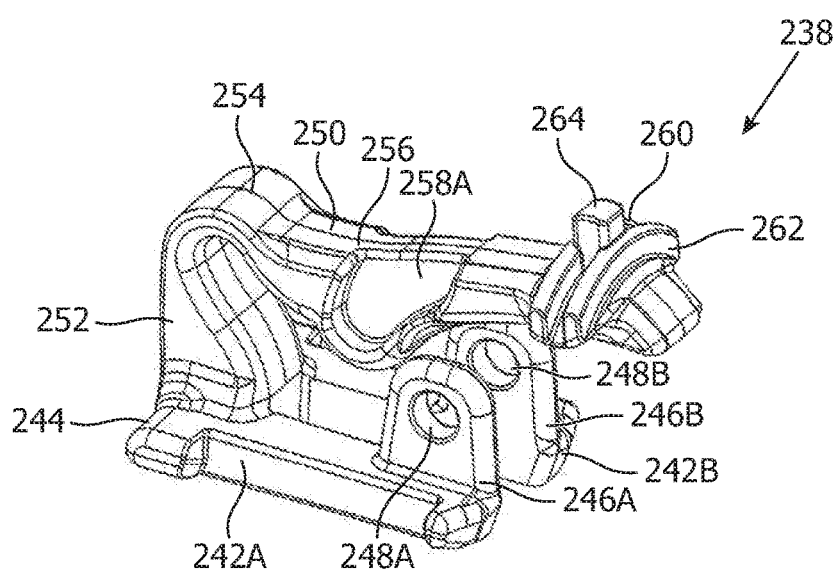
FIG. 23 is a front isometric view.
Figure 24:
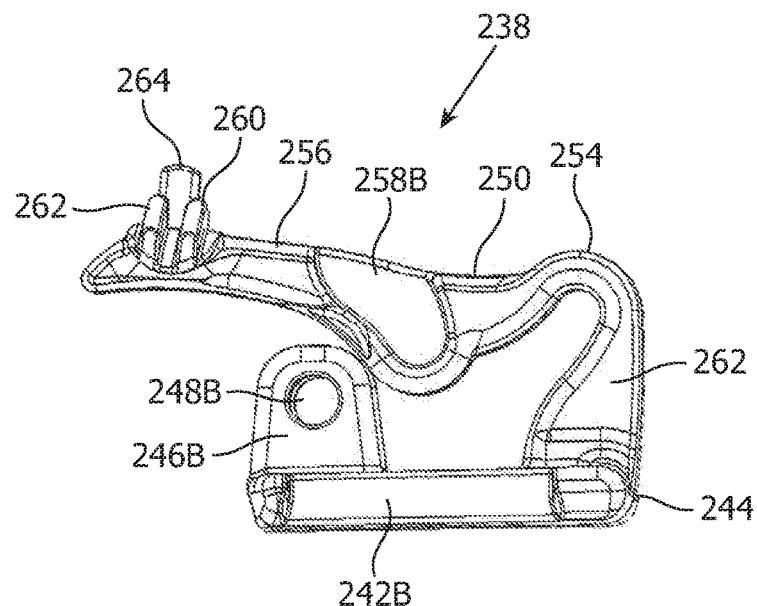
FIG. 24 is a left side elevational view.
Figure 25:
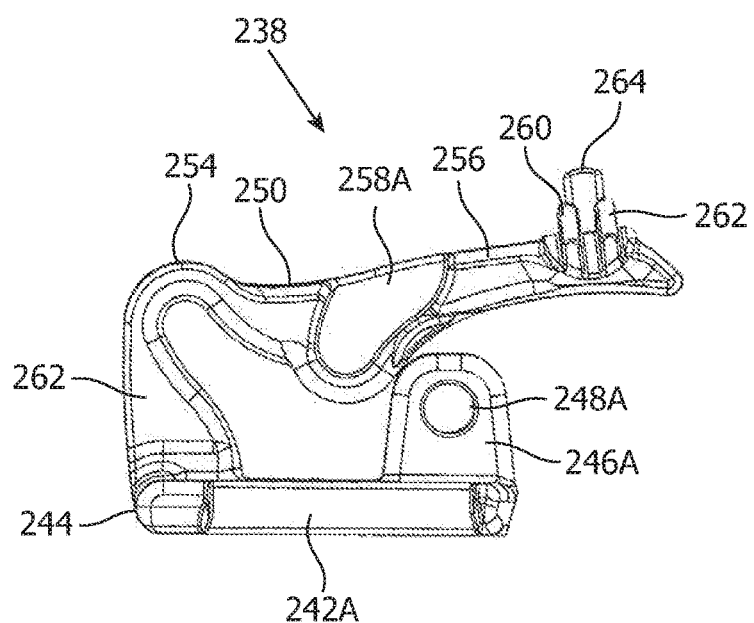
FIG. 25 is a right side elevational view of a base member of the button assembly shown in FIG. 22.

FIG. 23 is a front isometric view, FIG. 24 is a left side elevational view, and FIG. 25 is a right side elevational view of base member 238. Base member 238 includes a first foot member 242A and a second foot member 242B that are coupled to one another at a rear portion 244 of base member 238. A first projecting member 246A having a hole 248A extends upwardly from foot member 242A, and a second projecting member 246B having a hole 248B extends upwardly from foot member 242B.

An arm member 250 is coupled to rear portion 244. As seen in FIGS. 23 and 24, arm member 250 includes a base portion attached to and extending generally upwardly from rear portion 244. An arched portion 254 is attached to base portion 252. Finally, arm member 250 includes an extension portion 256 extending from arched portion 254. The shape and configuration of arched portion 254 causes it to act like a spring that biases extension portion 256 upwardly (away from first foot member 242A and a second foot member 242B). In addition, extension portion 256 includes a first side recess 258A provided in a first side thereof and a second side recess 258B provided in a second side thereof. The distal end of extension portion 256 further includes ridge members 260 and 262 that extend transversely to arm member 250. A post member 264 is positioned on extension portion in between ridge members 260 and 262.

Figure 26:
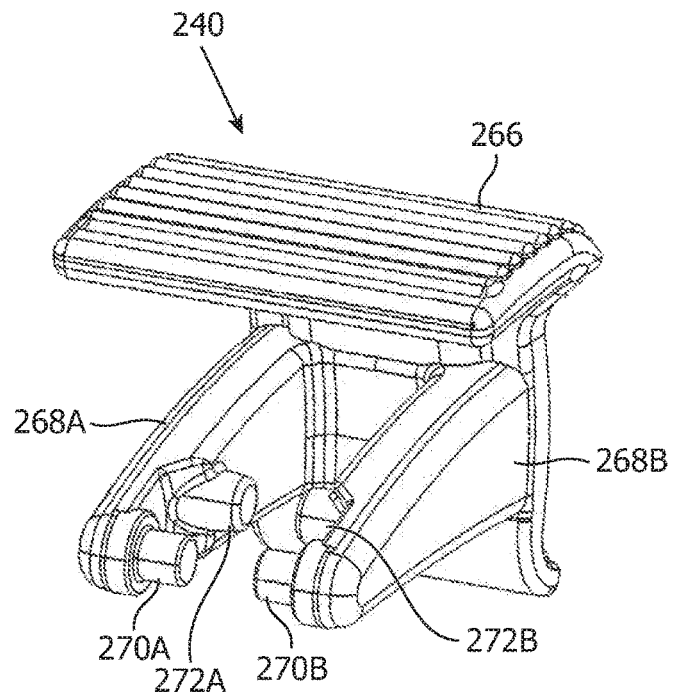
FIG. 26 is a front isometric view.
Figure 27:
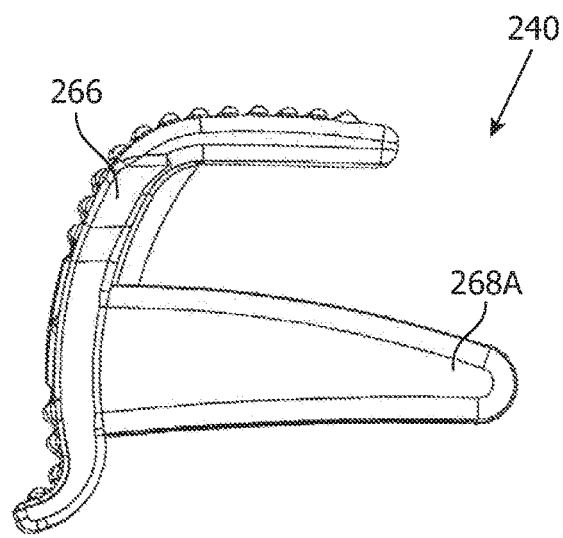
FIG. 27 is a side elevational view.
Figure 28:
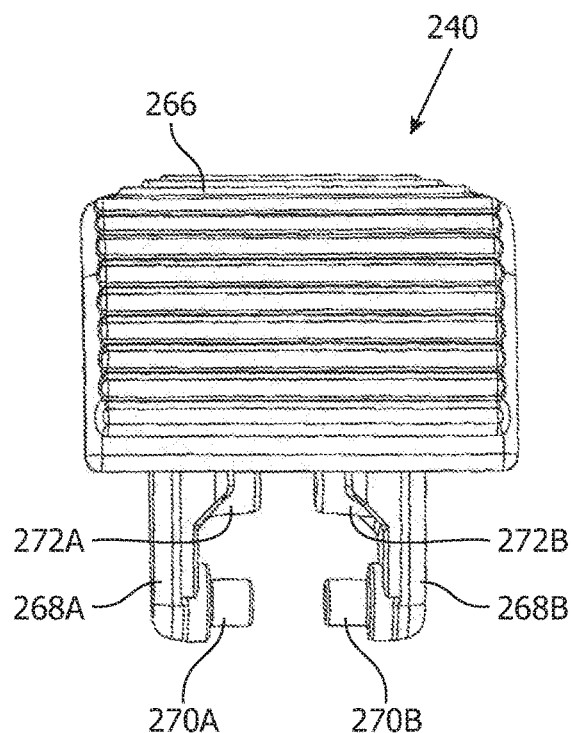
FIG. 28 is a top plan view and FIG. 29 is a rear elevational view of a button member of the button assembly shown in FIG. 22.
Figure 29:
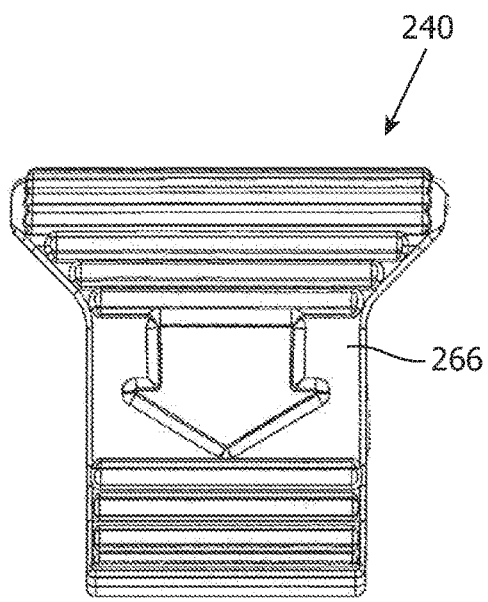

FIG. 26 is a front isometric view, FIG. 27 is a side elevational view, FIG. 28 is a top plan view and FIG. 29 is a rear elevational view of button member 240. Button member 240 includes a ribbed engagement member 266 structured to be engaged and pressed by a finger of the patient to actuate button assembly 226 as described elsewhere herein. First and second arms 268A and 268B extend outwardly from an inner surface of engagement member 266. Arm 268A includes an inwardly extending front peg 270A and an inwardly extending rear peg 272A, and similarly arm 268B includes an inwardly extending front peg 270B and an inwardly extending rear peg 272B.

Button assembly 226 is assembled by positioning button member 240 over base member 238 in a manner wherein rear peg 272A is received within side recess 258A and rear peg 272B is received within side recess 258B and inserting front peg 270A through hole 248A and front peg 270B through hole 248B. When so assembled, a downward force that is applied to engagement member 266 will cause button member to rotate about front pegs 270A, 270B, and the force applied to side recesses 258A, 258B by rear pegs 272A, 272B will cause arm member 250 to move downwardly in a cantilevered fashion against its normal bias. The significance of this is described below.

Adjustment mechanism 202 is assembled by inserting button assembly 226 into the rear of main channel 214 of housing 216 in a manner wherein foot members 242A and 242B are received in lower slot 216. When this is done, as seen in FIGS. 14 and 15, engagement member 266 will extend above the top surface of housing 206. Next, a downward force is applied to engagement member 266, thereby causing arm member 250 to move downwardly, and forehead cushion support member 224 is inserted into the front of housing 216. In particular, central post member 228 is inserted into main channel 214 of housing 216, and side post members 230A, 230B are inserted into first side channel 212A and second side channel 212B, respectively, of housing 206 (lower flanges 236A, 236B are received in slots 222A, 222B, respectively). The downward force on engagement member 266 is then released, causing arm member 250 to be biased upwardly. When this is done, post member 264 will be received through central orifice 234 of central post member 228, and ridge members 260, 262 will be received in the slots or recesses present on opposite sides of adjacent teeth 232A, 232B (FIG. 21). In such a condition, the position of forehead cushion support member 224 within housing 206 will be fixed. If it is desired to move forehead cushion support member 224 within housing 206, a downward force is again applied to engagement member 266, thereby causing arm member 250 to move downwardly out of engagement with teeth 232A, 232B, thereby permitting free movement of forehead cushion support member 224. When the desired position is achieved, the downward force is released so that arm member 250 will again engage teeth 232A, 232B.

Thus, when a patient interface device 8 is assembled with forehead support assembly 200, the position of housing 206 and connecting member 22 of frame member 16 relative to forehead cushion support member 224 and forehead cushion 204 (which will be at a fixed position on the patient's head) can be linearly adjusted by operation of the adjustment mechanism 202 as just described. This linear adjustment action allows for selective adjustment of the force that is applied to the bridge of the patient's nose by the apex portion of cushion 14 because varying the position of connecting member 22 as just described will cause the apex portion of cushion 14 to rotate toward and away from the patient's nose.

Figure 30:
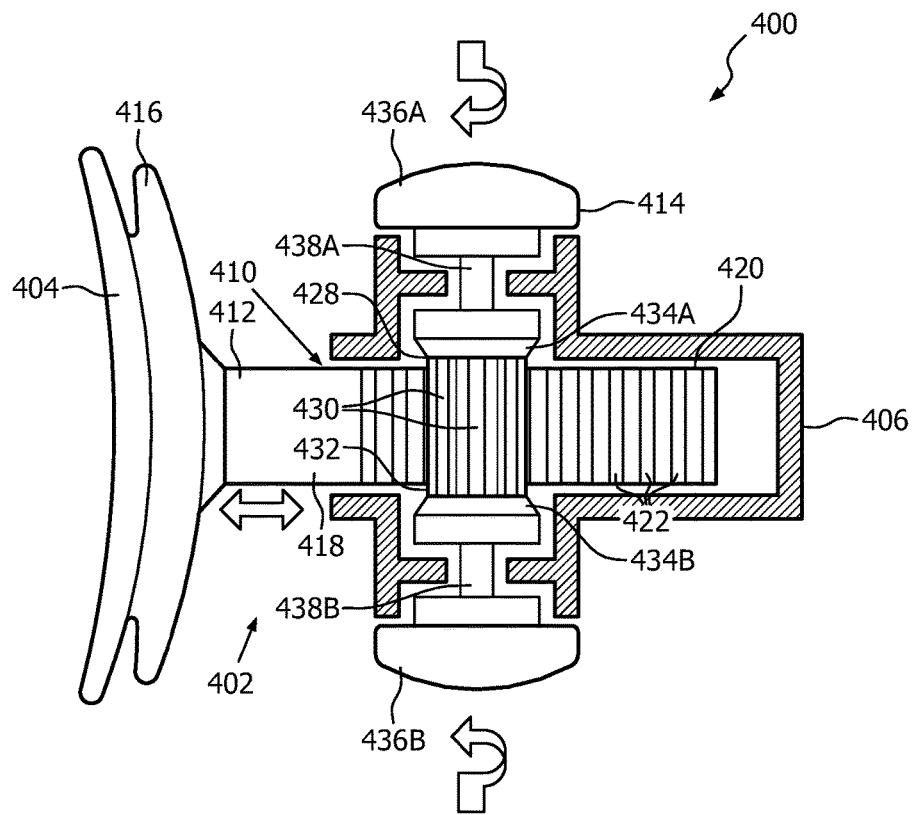
FIGS. 30 and 32 are top plan views in partial cross-section and FIGS. 31 and 33 are side views in partial cross-section of an adjustable forehead support assembly according to yet a further alternative embodiment of the present invention.
Figure 31:
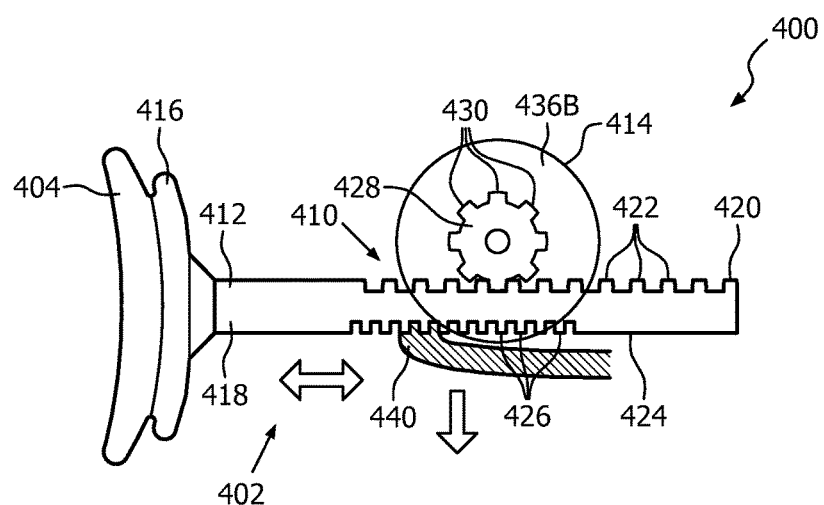

FIG. 30 is a top plan view in partial cross-section and FIG. 31 is a side elevational view in partial cross-section of an adjustable forehead support assembly 400 according to a further alternative embodiment of the present invention. Adjustable forehead support assembly 400 may be substituted for adjustable forehead support assembly 28 of patient interface device 8 in system 2. Adjustable forehead support assembly 400 includes an adjustment mechanism 402 that is coupled to a forehead cushion 404.

Adjustment mechanism 402 includes a housing portion 406 structured to be coupled to the distal end of a frame member as described elsewhere herein. Housing portion 406 may be formed as an integral part of the frame member or may be formed separately and attached to the frame member by a suitable mechanism such as an adhesive. Adjustment mechanism 402 also includes a linear translation assembly 410 (described in greater detail below) partially received and housed within housing portion 406.

Linear translation assembly 410 includes a forehead cushion support member 412 and a knobbed actuator 414. Forehead cushion support member 412 includes a base portion 416 to which forehead cushion 404 is attached, and an elongated post member 418 extending from base portion 416. In the exemplary embodiment, post member 418 includes a top gear train 420 (also known as a rack) including a number of teeth 422 provided on the top surface of post member 418 and a bottom gear train 424 (also known as a rack) including a number of teeth 426 provided on the bottom surface of post member 418.

Knobbed actuator 414 includes a central pinion member 428 having a number of teeth 430 provided on a cylindrical central portion 432 thereof and first and second ramped portions 434A, 434B provided on opposite sides of the central portion 432. Teeth 430 are structured to mesh and cooperate with teeth 422 of gear trains 420. As seen in FIG. 30, knobbed actuator 414 includes first and second knob members 436A, 436B that are attached to first and second ramped portions 434A, 434B, respectively, by posts 438A, 438B. In the illustrated, non-limiting embodiment, ramped portions 434A, 434B are angled at 45 degrees. Finally, housing portion 406 includes a flexible pawl member 440 that is structured to selectively engage teeth 426. Pawl member 440 is biased toward the bottom surface of post member 418.

Figure 32:
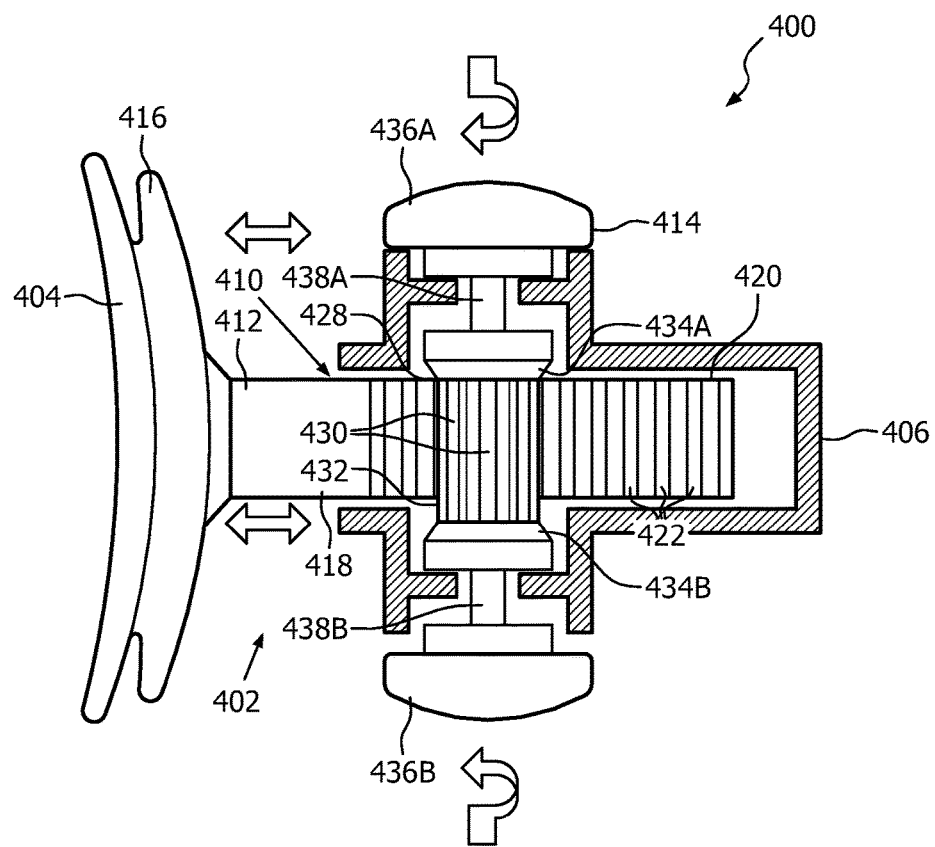
Figure 33:
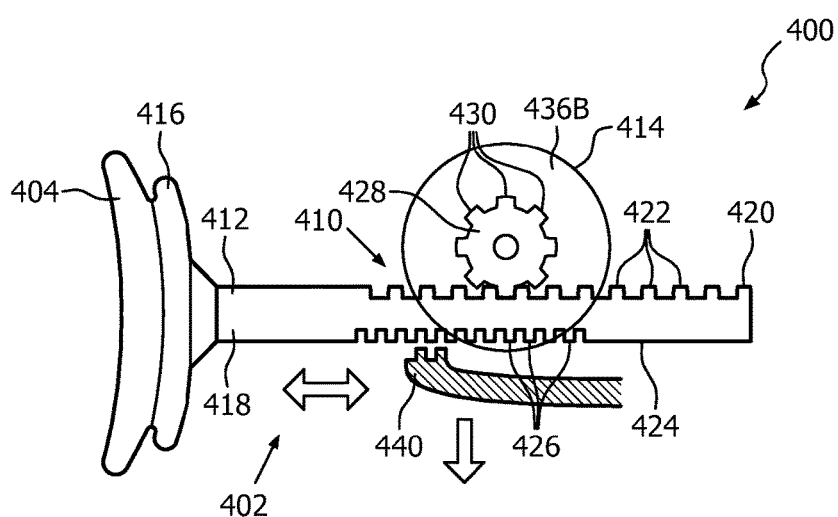

FIGS. 30 and 31 show adjustment mechanism 402 in a locked condition wherein pawl member 440 is engagement with gear train 424. In such a condition, knobbed actuator 414 in unable to be rotated in the direction of the arrows shown in FIG. 30, and thus housing portion 406 is not able to be moved relative to forehead cushion support member 412 and forehead cushion 404 (which will be at a fixed position on the patient's head). Conversely, FIGS. 32 and 33 show adjustment mechanism 402 in an unlocked condition wherein pawl member 440 is forced out of engagement with gear train 424 as described below. In the unlocked condition, knobbed actuator 414 is able to be rotated in the direction of the arrows shown in FIG. 32, and thus housing portion 406 is able to be moved relative to forehead cushion support member 412 and forehead cushion 404.

More specifically, in order to move adjustment mechanism 402 to the unlocked condition, a user must press inwardly on either one of the knob members 436A, 436B. Doing so will cause the central pinion member 428 to move transversely across post member 418 as seen in FIG. 32 (wherein the knob member 436A has been pushed inwardly). Such transverse movement will in turn cause the ramped portion 434A, 434B that is associated with the one of the knob members 436A, 436B that was pushed inwardly (ramped portion 434A in the illustrated embodiment) to engage a feature of housing portion 406 that is coupled to pawl member 440 and thereby force pawl member away from the bottom surface of post member 418 (against the bias). When this is done, knobbed actuator 414 can be freely rotated. Such rotation will, through interaction between pinion member 428 and gear train 420, cause the position of housing portion 406 and the attached frame member relative to forehead cushion support member 412 and forehead cushion 404 (which will be at a fixed position on the patient's head) to be linearly adjusted, thereby allowing for selective adjustment of the force that is applied to the bridge of the patient's nose as described elsewhere herein. When the inward pressure on the one of the knob members 436A, 436B is released, adjustment mechanism 402 will be biased back into the locked condition shown in FIGS. 30 and 31.

In the claims, any reference signs placed between parentheses shall not be construed as limiting the claim. The word "comprising" or "including" does not exclude the presence of elements or steps other than those listed in a claim. In a device claim enumerating several means, several of these means may be embodied by one and the same item of hardware. The word "a" or "an" preceding an element does not exclude the presence of a plurality of such elements. In any device claim enumerating several means, several of these means may be embodied by one and the same item of hardware. The mere fact that certain elements are recited in mutually different dependent claims does not indicate that these elements cannot be used in combination.

Although the invention has been described in detail for the purpose of illustration based on what is currently considered to be the most practical and preferred embodiments, it is to be understood that such detail is solely for that purpose and that the invention is not limited to the disclosed embodiments, but, on the contrary, is intended to cover modifications and equivalent arrangements that are within the spirit and scope of the appended claims. For example, it is to be understood that the present invention contemplates that, to the extent possible, one or more features of any embodiment can be combined with one or more features of any other embodiment.

What is claimed is:

1. A patient interface device, comprising:
 (a) a patient sealing assembly adapted to communicate a flow of breathing gas within an airway of a patient, the patient sealing assembly including a cushion and a frame member coupled to the cushion; and
 (b) an adjustable forehead support assembly provided at a distal end of the frame member, the adjustable forehead support assembly including an adjustment mechanism coupled to a forehead cushion, the adjustment mechanism including:
  (i) a housing, (ii) a forehead cushion support member having a base portion coupled to the forehead cushion and an elongated post member extending from the base portion and received within the housing, and
  (iii) a locking member structured to be selectively coupled to the elongated post member, the locking member being moveable between a locked condition and an unlocked condition, wherein in the locked condition the locking member engages the elongated post member and prevents the elongated post member from moving relative to the housing, and wherein in the unlocked condition the locking member does not engage the elongated post member such that the elongated post member and the housing are freely linearly movable with respect to one another in a direction along a longitudinal axis of the elongated post member without any spring bias being applied to the elongated post member along the longitudinal axis, wherein movement of the elongated post member relative to the housing causes movement of the frame member and the cushion relative to the forehead cushion, and wherein the locking member includes an elastic member held within the housing and a button member having an engagement portion and a looped portion defining a first orifice extending downwardly from the engagement portion, wherein the looped portion is received within the housing through a second orifice provided in the housing and engages the elastic member, wherein the elongated post member is received through the first orifice, and wherein the locking member is moved to the unlocked condition responsive to a force being applied to the engagement portion causing the elastic member to be compressed.

2. The patient interface device according to claim 1, wherein when the patient interface device is donned by the patient, movement of the frame member and the cushion relative to the forehead cushion will adjust a force applied to a bridge of a nose of the patient by an apex portion of the cushion by causing the cushion to pivot relative to the patient's nose.

3. The patient interface device according to claim 1, wherein the elastic member is made of silicone.

4. The patient interface device according to claim 1, wherein the elastic member includes a central portion having rounded top surface having a recess provided therein, wherein a bottom of the looped portion is received within the recess.

5. The patient interface device according to claim 1, wherein the housing includes a bottom slot having first and second end slot portions, wherein the elastic member includes first and second outwardly extending flanges provided on opposites sides of a bottom surface thereof, and wherein the first outwardly extending flange is received in the first end slot portion and the second outwardly extending flange is received in the second end slot portion.

6. The patient interface device according to claim 1, wherein the elongated post member includes a plurality of recesses along a length thereof, wherein the looped portion includes a projecting member structured to be received within one of the recesses when the elastic member is not compressed such that the locking member is in the locked condition, and wherein when the force is applied to the engagement portion causing the elastic member to be compressed, the projecting member will not be received within any of the recesses, such that the locking member is in the unlocked condition thereby permitting the elongated post member to be moved within the button member.

7. The patient interface device according to claim 1, wherein the elongated post member includes a plurality of first side recesses on a first side thereof, a plurality of second side recesses on a second side thereof, and a plurality of bottom recesses on a bottom surface thereof, wherein the looped portion includes a bottom projecting member structured to be received within one of the bottom recesses when the elastic member is not compressed, a first side projecting member structured to be received within one of the first side recesses when the elastic member is not compressed, and a second side projecting member structured to be received within one of the first side recesses when the elastic member is not compressed, and wherein when the force is applied to the engagement portion causing the elastic member to be compressed, the bottom projecting member will not be received within any of the bottom recesses, the first side projecting member will not be received within any of the first side recesses, and the second projecting member will not be received within any of the second side recesses, thereby permitting the post member to be moved within the button member.

8. The patient interface device according to claim 1, wherein the housing includes one or more receiving slots structured to receive and guide the looped portion of the button member.

9. A patient interface device, comprising:
 a patient sealing assembly adapted to communicate a flow of breathing gas within an airway of a patient, the patient sealing assembly including a cushion and a frame member coupled to the cushion; and
 an adjustable forehead support assembly provided at a distal end of the frame member, the adjustable forehead support assembly including an adjustment mechanism coupled to a forehead cushion, the adjustment mechanism including a housing and a forehead cushion support member having a base portion coupled to the forehead cushion and an elongated post member extending from the base portion and received within the housing, wherein the housing includes a rear end having a rear orifice and a pawl member, wherein the elongated post member is received through the rear orifice and includes a first gear train and a second gear train each provided along at least a portion of a length of the elongated post member, wherein the adjustment mechanism further includes a knobbed actuator having a pinion member, wherein the pinion member is in operative engagement with the first gear train, wherein the pawl member is biased to normally be in engagement with the second gear train, wherein movement of the knobbed actuator in a direction transverse to a longitudinal axis of the elongated post member causes the pawl member to be moved out of engagement with the second gear train such that rotation of the knobbed actuator causes relative movement between the elongated post member and the housing along a longitudinal axis of the elongated post member, and wherein movement of the elongated post member relative to the housing causes movement of the frame member and the cushion relative to the forehead cushion.

10. The patient interface device according to claim 9, wherein the pinion member includes a ramped portion, wherein when the knobbed actuator is moved in the transverse direction the ramped portion causes a force to be provided against the biasing of the pawl member such that the pawl member is moved out of engagement with the second gear train.

* * * * *